United States Patent [19]
Lawless

[11] Patent Number: 6,105,440
[45] Date of Patent: Aug. 22, 2000

[54] PORTABLE AIR SAMPLING SYSTEMS INCLUDING NON-INTRUSIVE ACTIVITY MONITOR AND METHODS OF USING SAME

[75] Inventor: Philip A. Lawless, Durham, N.C.

[73] Assignee: Research Triangle Institute, Research Triangle Park, N.C.

[21] Appl. No.: 09/268,761

[22] Filed: Mar. 16, 1999

[51] Int. Cl.[7] .................................................. G01N 1/00
[52] U.S. Cl. .................................... 73/863.21; 73/864.34
[58] Field of Search ........................... 73/863.01, 863.21, 73/863.23, 864.34

[56] References Cited

U.S. PATENT DOCUMENTS

| | | |
|---|---|---|
| 3,838,684 | 10/1974 | Manuel et al. . |
| 3,898,981 | 8/1975 | Basham . |
| 3,956,940 | 5/1976 | Guild .................................. 73/421.5 R |
| 4,080,832 | 3/1978 | Moody et al. ...................... 73/421.5 R |
| 4,091,674 | 5/1978 | Amey ................................. 73/421.5 R |
| 4,183,247 | 1/1980 | Allen et al. ........................ 73/421.5 R |
| 4,187,836 | 2/1980 | Allen et al. ........................ 128/200.24 |
| 4,187,859 | 2/1980 | Allen et al. .............................. 128/725 |
| 4,202,212 | 5/1980 | Allen et al. ........................ 73/421.5 R |
| 4,375,667 | 3/1983 | Buchan ................................... 364/418 |
| 4,389,903 | 6/1983 | Bertone et al. ....................... 73/863.03 |
| 4,474,185 | 10/1984 | Diamond . |
| 4,589,292 | 5/1986 | Delhaye et al. . |
| 4,721,517 | 1/1988 | Cloutier ................................... 55/270 |
| 4,747,315 | 5/1988 | Padden .................................. 73/863.01 |
| 5,000,052 | 3/1991 | Sipin .................................... 73/863.03 |
| 5,012,196 | 4/1991 | Baranski . |
| 5,052,400 | 10/1991 | Dietz . |
| 5,107,713 | 4/1992 | Peck et al. ............................ 73/863.02 |
| 5,119,682 | 6/1992 | Bellinger .............................. 73/864.73 |
| 5,163,818 | 11/1992 | Betsill et al. ............................. 417/18 |
| 5,201,231 | 4/1993 | Smith .................................... 73/863.22 |
| 5,333,511 | 8/1994 | Boyum et al. ........................ 73/864.34 |
| 5,553,508 | 9/1996 | Dabberdt et al. ....................... 73/63.02 |
| 5,602,734 | 2/1997 | Kithil . |
| 5,724,024 | 3/1998 | Sonderegger et al. . |
| 6,014,602 | 1/2000 | Kithil et al. . |

*Primary Examiner*—Robert Raevis
*Attorney, Agent, or Firm*—Myers Bigel Sibley & Sajovec, PA

[57] ABSTRACT

Portable air sampling systems and methods are provided for intermittently sampling air in the breathing zone of a person over extended periods of time. Air sampling system performance can be continuously measured and recorded within a data logger. In addition, physical activity levels of a person wearing a portable air sampling system can be continuously monitored and recorded within the data logger. Air sampling system performance monitoring includes measuring pressure drop across a filter and measuring temperature of air flowing through the filter. Physical activity levels of a person can be monitored easily and non-intrusively by measuring changes in electrical capacitance of a transducer maintained in close proximity to the person.

29 Claims, 6 Drawing Sheets

PORTABLE AIR SAMPLING SYSTEMS INCLUDING NON-INTRUSIVE ACTIVITY MONITOR AND METHODS OF USING SAME

FIELD OF THE INVENTION

The present invention relates generally to air sampling and, more particularly, to portable air sampling systems and methods.

BACKGROUND OF THE INVENTION

Personal air sampling devices can be used to determine the exposure of individuals to various airborne particles and contaminants over a period of time. For example, U.S. Pat. No. 4,721,517 to Cloutier and U.S. Pat. No. 5,119,682 to Bellinger each describe sampling devices configured to be worn by an individual and to obtain air samples within the breathing zone of the wearer. Sampled air is pumped through a filter which retains any airborne particles and/or contaminants. Subsequently, the filter can be weighed or subjected to other types of analysis in order to determine the nature of the collected particles and/or contaminants.

Air flow requirements for air sampling are conventionally based on the expected concentration of airborne particles, and the ability to measure and analyze the particles collected. Collection of too much particulate material can clog a filter and can cause a sampling flow rate to drop below acceptable levels. Sampling pumps for personal sampling systems conventionally operate at a fixed flow rate and with size-selective sampling inlets. Sampling periods are conventionally based upon the amount of particulate material collected. For example, shorter sampling periods may be used within environments having a higher average concentration of airborne particles.

In order to reduce inconvenience to a wearer, conventional personal air sampling devices typically are designed to be as small and as lightweight as possible. To facilitate portability, personal air sampling devices are conventionally battery powered. However, batteries may have a limited lifetime which can result in sampling periods that are not long enough to obtain a satisfactory air sample. In order to extend air sampling periods, intermittent air sampling can be performed wherein a sampling pump is operated intermittently, creating "ON" periods and "OFF" periods. (See, for example, U.S. Pat. No. 5,201,231 to Smith and U.S. Pat. No. 4,080,832 to Moody et al.). Intermittent air sampling can extend battery life so that air sampling can be extended over a longer time period than achievable via continuous air sampling. Intermittent air sampling also facilitates obtaining representative aerosol samples over an extended period of time without "blinding" a filter by collecting too much particulate matter.

It would be valuable to independently verify that an air sampling device was worn by an individual during a time period designated for sampling (i.e., an ON period during intermittent operation). Unfortunately, conventional personal air sampling devices designed for intermittent operation may not provide an accurate way of ensuring that an individual is wearing a device during an ON period. Also, it would be valuable to know the level of physical activity of the wearer of an air sampling device during sampling because an inhaled dose of airborne particles may be a function of breathing rate as well as of sampling time.

It is known to sample air in proportion to the actual respiration of an individual. For example, in U.S. Pat. No. 4,183,247 to Allen et al., a sampling pump is activated by the expansion and contraction of an individual's thoracic cavity during respiration. In addition, it is known to sample air in proportion to the pulmonary output of an individual. For example, U.S. Pat. No. 4,589,292 to Delhaye et al. describes a process and device for sampling ambient air in proximity of the respiratory track of an individual wherein a sampling pump is piloted by a signal indicating the individual's cardiac rhythm, such as from the pulsed flow of blood in an ear lobe of the individual. Unfortunately, existing methods of monitoring physical activity of a person are somewhat personally intrusive and complex.

SUMMARY OF THE INVENTION

In view of the above, it is therefore an object of the present invention to provide personal air sampling devices that can operate autonomously over extended periods of time without inconvenience to the wearer.

It is another object of the present invention to provide personal air sampling devices that can monitor various air sampling system performance criteria.

It is another object of the present invention to provide personal air sampling devices that can verify that a device was worn properly by an individual during sampling.

It is another object of the present invention to provide a way of monitoring the physical activity of a person that can be less complex and personally intrusive.

These and other objects of the present invention are provided by portable air sampling systems and methods for intermittently sampling air in the breathing zone of a person over extended periods of time, wherein both air sampling performance and physical activity of the person can be continuously monitored. Air sampling methods according to the present invention include intermittently sampling air from the breathing zone of a person by drawing the air through a filter via a sampling pump. Pressure drop across the filter and the temperature of the air flowing through the filter can be continuously measured and recorded in a data logger. Other pump performance characteristics can be measured, as well. For example, voltage across a power supply that provides electric power to a pump motor can be continuously monitored. In addition, physical activity levels of a person wearing the air sampling device can be monitored easily and non-intrusively by measuring changes in electrical capacitance of a transducer maintained in close proximity to the person.

According to an embodiment of the present invention, a small, lightweight pack, such as a fanny pack, can be configured to house various air sampling and activity monitoring components. A filter device can be mounted on the outside of the pack to sample air in the breathing zone of the person. The filter device includes a housing having an air inlet, an air outlet, and a filter element disposed within the housing. The filter element is configured to retain particles entrained within air flowing therethrough.

A sampling pump disposed within the pack, is in fluid communication with the filter device air outlet. The sampling pump is configured to draw a predetermined volume of air from the breathing zone of the wearer into the filter device and through the filter element. A timing circuit is provided with the pump for intermittently activating the sampling pump to draw the predetermined volume of air through the filter element at predetermined intervals.

Also included within the pack are various systems for monitoring air sampling system performance. For example, pressure drop across the filter and the temperature of air passing through the filter are continuously monitored and recorded in a data logger. In addition, voltage across a pump motor power supply can also be monitored on a continuous basis.

Also included within the pack is an activity monitoring system for monitoring the physical activity of the person wearing the pack. A transducer, comprising a pair of adjacent capacitor plates, is configured to change electrical capacitance in response to a change in distance from each plate to the body of the person wearing the pack. Changes in electrical capacitance of the transducer are then recorded in the data logger.

Thus, a system according to the present invention can intermittently pump air through a filter mechanism, can perform real-time logging of system performance, and can directly measure the activity levels of an individual wearing the system. The present invention is advantageous because the air sampling system is designed to be lightweight and convenient for a person to wear. Furthermore, intermittent air sampling includes a pattern of ON and OFF pump operation periods that can extend battery life so that a longer sampling period can be obtained than with continuous pump operation. Intermittent sampling can also make it possible to obtain representative air samples over an extended period of time with a reduced risk of clogging the filter with too much particulate material.

According to another embodiment of the present invention, a non-intrusive apparatus for monitoring the physical activity levels of a person is provided. A data logger, configured to fit within a pocket of an article of clothing worn by the person, includes a pair of capacitor plates mounted thereto that are configured to change electrical capacitance in response to changes in distance from each capacitor plate to the body of the person. The data logger is configured to record changes in electrical capacitance of the capacitor plates. This aspect of the present invention is particularly advantageous because monitoring can be personally less intrusive than other known methods.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Intermittent Sampling System

Figure 1:
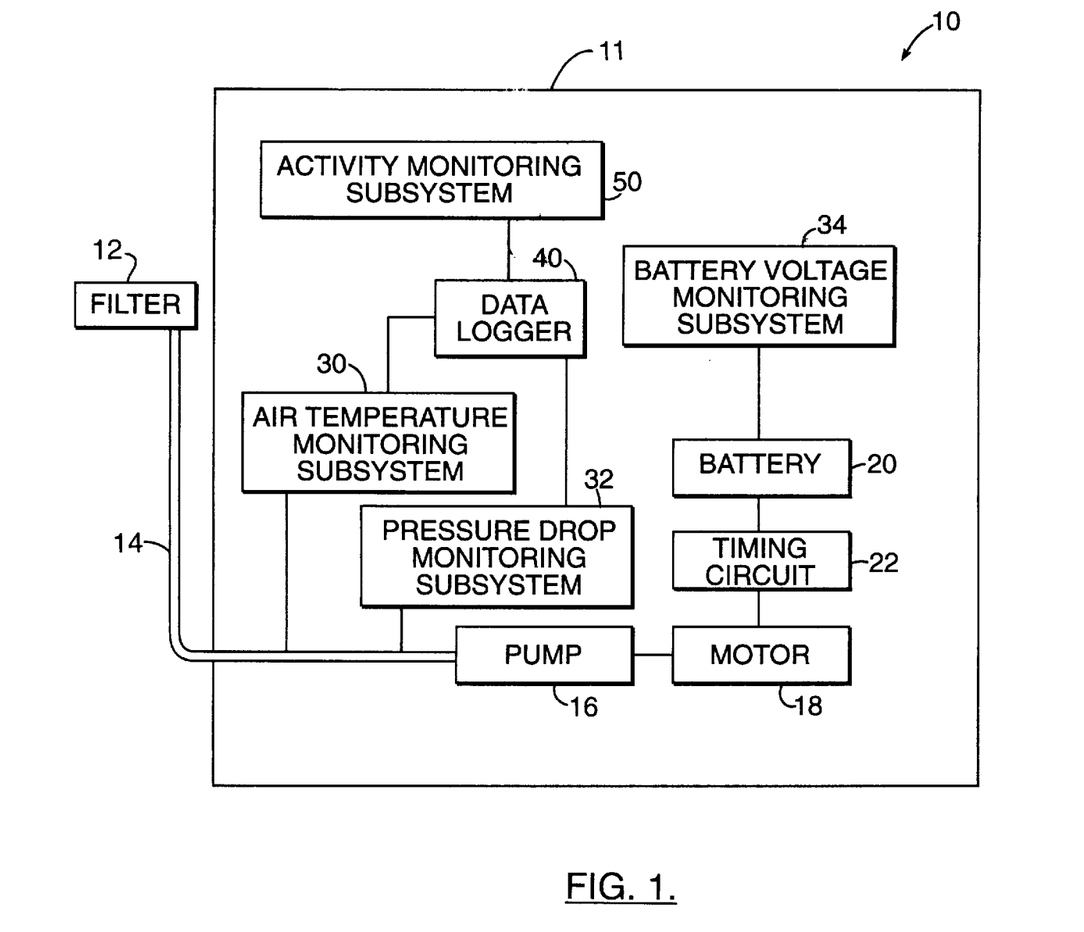
FIG. 1 schematically illustrates a portable, intermittent sampling system including performance monitoring and activity monitoring subsystems, according to the present invention.

Referring now to FIG. 1, a portable, intermittent air sampling system 10 for sampling air in the breathing zone of a person for extended periods of time, for monitoring various sampling operations, and for monitoring the physical activity of a person, according to the present invention, is schematically illustrated. It is understood that the present invention is not limited to sampling air in breathing zones of human beings. The present invention may be utilized to sample air in the breathing zone of any creature, including animals.

Preferably, the various components of the sampling system 10 are contained within, or attached to the outside of, an enclosure 11 that is designed to be worn by a person with minimal inconvenience. A filter 12, preferably located on the outside of the enclosure 11, is configured to sample air within the breathing zone of an individual wearing the enclosure 11. It is understood, however, that the filter 12 could also be located on or within the enclosure 11. The term "breathing zone of an individual" is defined as the immediate area surrounding a person. A tube 14 has one end in fluid communication with the filter 12 and an opposite end in fluid communication with a pump 16, as illustrated. A sampling pump 16 draws air through the filter 12 via the sampling tube 14 such that airborne particles and/or contaminants are captured by the filter 12.

An exemplary sampling pump for use according to the present invention is a BGI Model AFC-123 constant speed pump (BGI, Inc., 58 Guinan St., Waltham, Mass. 02154), wherein speed is maintained by a feedback circuit. An exemplary filter for use according to the present invention is a low pressure drop commercial filter manufactured by Gelman Sciences, 600 South Wagner Rd., Ann Arbor, Mich. 48106.

Sampling pumps utilized in accordance with the present invention conventionally draw between about 2 and 4 liters per minute (2–4 l/min). Accordingly, for an average airborne particulate concentration of 50 micrograms per cubic meter ($\mu g/m^3$), a sampling period for a sampling pump operating at 2 l/min would be between about 1,000 and 20,000 minutes (0.7–14 days). As would be understood by those skilled in this art, higher average concentrations of airborne particulates could result in shorter sampling periods.

Sampling pumps and filters for use with personal air sampling devices are well known in this art and need not be described further herein. Preferably the sampling pump 16 is a low-power, battery operated pump. Furthermore, it is to be understood that the present invention may be utilized with various types of sampling pumps and filters.

Air flow requirements for sampling air within the breathing zone of an individual are typically determined by the expected concentration of airborne particles and the ability to measure the particulate material collected in a filter. For example, if the expected concentration is 50 $\mu g/M^3$ and the filter weighing precision is 10 $\mu g$, then 2 $m^3$ of air should be sampled to obtain a ten-to-one signal to noise ratio. On the other hand, too much particulate material can clog a filter (referred to as "blinding") and can cause the air flow rate to drop to unacceptably low levels. The amount of particulate material that causes blinding depends on both the type of filter used and the type of airborne particles. Often, however, several milligrams of particulate material are sufficient to cause blinding. As a result, a preferred range of collected particulate material is between about 100 μg and 2,000 μg.

Still referring to FIG. 1, the sampling pump 16 is driven by a motor 18 which receives power from a battery 20. Sampling pump motors are well known to those skilled in this art and need not be described further herein. The battery 20 may be any of various chemical types including, but not limited to, nickel-cadmium, carbon-zinc, alkaline, mercury and lithium. In addition, the battery 20 may have various physical dimensions including, but not limited to, AAA, AA, C, and D sizes.

A timing circuit 22 is preferably utilized to implement intermittent sampling, and thereby extend the sampling period. The timing circuit 22 provides power to the motor 18 which operates the pump 16 during designated sampling periods at a normal flow rate. The timing circuit 22 thus conserves battery power by preventing the pump 16 from operating between designated sampling periods. By using intermittent sampling, it is possible to extend the life of the battery 20 and the sampling period. Furthermore, it is also possible to obtain representative airborne particle samples over an extended period of time without running the risk of blinding the filter 12 by collecting too much particulate matter. For example, by operating a sampling pump for one minute every three minutes, the sampling period obtainable with a given battery would be at least three times as long as for continuous operation, both in terms of battery capacity and filter blinding. Regarding battery capacity, the advantage should be greater than three times because it is known that batteries recover some of their capacity when not being discharged.

Figure 2:
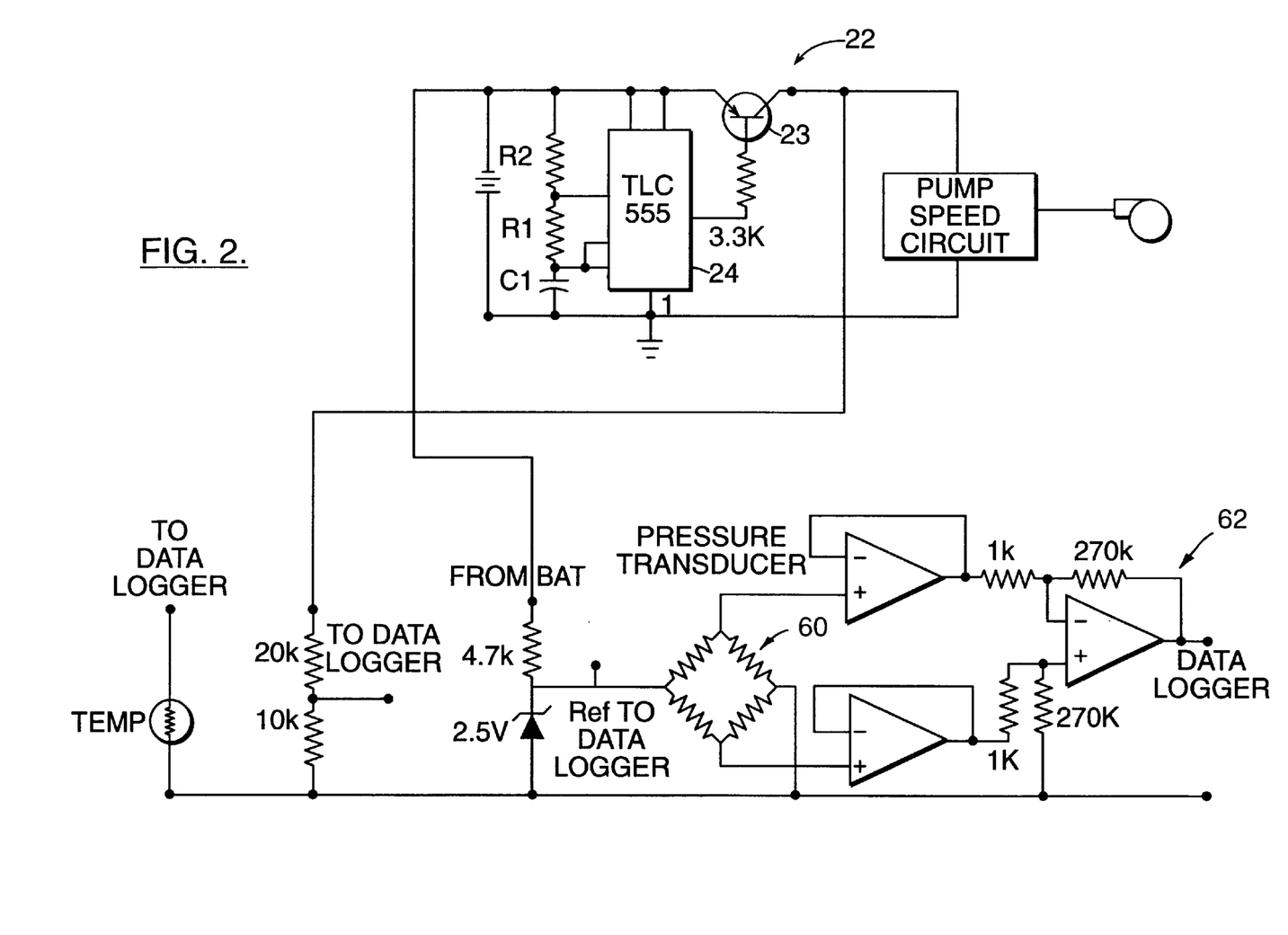
FIG. 2 illustrates a timing circuit for use with a low-power, battery operated sampling pump and preferred circuits for providing various sampling system monitoring signals to a data logger, according to the present invention.

A preferred timing circuit 22 for use with the present invention present invention is illustrated in FIG. 2. The illustrated timing circuit 22 utilizes a saturated transistor 23 to provide a low voltage-drop switch. The transistor 23 is preferably driven by a TL555C CMOS integrated circuit timer 24. The CMOS version of the integrated circuit timer 24 provides low power drain and high input impedances. The timing is controlled by resistors $R_1$, $R_2$ and capacitor $C_1$. For $R_1=R_2=8.2$ million ohms (8.2 MΩ) and $C_1=10$ microfarads (μF), each ON period is approximately 60 seconds and each OFF period is approximately 120 seconds. The duration of an ON and OFF period can be determined by component tolerances. The ratio ON:OFF is determined by the resistor values according to the equation:

$$\frac{t_{On}}{t_{Off}} = \frac{R_1}{R_1 + R_2}$$

Pump Monitoring Subsystems

Referring back to FIG. 1, an air temperature monitoring subsystem 30 is provided to monitor the temperature of air flowing through the filter 12. As is understood by those skilled in this art, changes in air temperature cause air density changes which affects the mass flow of air. According to the present invention, the flow rate of the sampling pump 16 is adjusted to compensate for changes in air temperature detected by the air temperature monitoring subsystem 30.

Preferably the temperature monitoring subsystem 30 comprises a calibrated thermistor that is in communication with the air flowing through the tube 14. As is known to those skilled in this art, thermistors are electronic sensing devices that change their resistance with changes in temperature. The resistance of the thermistor (temperature monitoring subsystem 30) is monitored by a data logger 40. As is known by those skilled in this art, a data logger is a device configured to measure any number of variables and make a written tabulation and/or record in a form suitable for computer input. A preferred data logger is an ACR Systems, Inc. Smart Reader 4 (ACR Systems, Inc., 12960 84th Ave., Surrey, British Columbia, Canada V3W1K7).

A pressure drop monitoring subsystem 32 is also provided to measure the drop in air pressure across the filter 12. Pressure drop across the filter 12 can provide an indication of air flow rate stability and whether filter blinding has occurred. Filter pressure is preferably measured with a semiconductor strain-gage bridge 60 and operational amplifier 62 that feeds the data logger 40, as illustrated in FIG. 2. Preferably, the pressure drop subsystem 32 is operated continuously to measure pressure at zero air flow (i.e., during pump OFF periods) and at full air flow (i.e., during pump ON periods). Continuous measuring of pressure drop across the filter 12 can facilitate detection of proper operation of the bridge 60 and amplifier 62, and verification that a proper intermittent sampling ON:OFF ratio is followed. Continuous measuring of pressure drop across the filter 12 also facilitates verifying that air is moving through the filter 12 and that the pump 16 is running.

A battery voltage monitoring subsystem 34 is provided to monitor the sampling pump battery voltage as controlled by the timing circuit 22. The battery voltage under load is recorded and the proper operation of the timing circuit 22 in terms of ON:OFF ratio and ON time duration is monitored by the battery voltage monitoring subsystem 34.

Activity Monitoring Subsystem

Referring back to FIG. 1, an activity monitoring subsystem 50 is provided that can detect and record physical motions of an individual wearing an air sampling apparatus according to the present invention. The recorded activity of the monitored individual may be used to verify that the personal sampling system was worn during proper time periods (i.e., during ON periods). Furthermore, the recorded activity of the monitored individual can provide an indication of the general degree of activity that the monitored individual was engaged in during a sampling period. Preferably, the activity monitoring subsystem 50 is based upon the capacitance measuring channel of the data logger 40.

Figure 3:
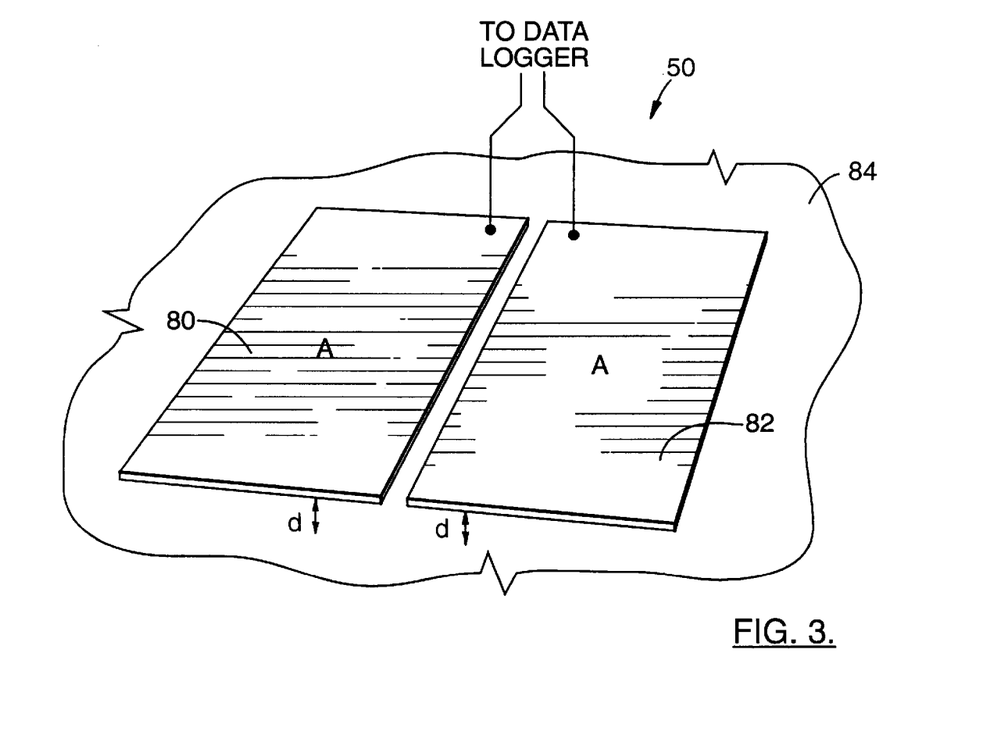
FIG. 3 illustrates an activity monitoring subsystem according to an embodiment of the present invention.

Referring now to FIG. 3, an activity monitoring subsystem 50 according to an embodiment of the present invention preferably includes a pair of insulated capacitor plates 80, 82 in communication with a data logger 40. The presence of an object, such as a human body 84, near the plates 80, 82 changes the capacitance between the plates 80, 82 which can be measured. If the plates 80, 82 have identical areas A and the distances from each of the plates 80, 82 to the body 84 are equal to d, then the capacitance can be measured as follows:

$$C_{measured} = C_\infty + \frac{1}{2} \in \frac{A}{d}$$

$C_{measured}$ is the value with the capacitor plates 80, 82 near the body 84 of an individual in farads (F). $C_\infty$ is the value with the plates far from the body 84 of an individual in farads (F). ε is the permittivity of the medium between the plates 80, 82 and the body 84 of an individual in farads per meter (F/m).

As an individual wearing the air sampling system 10 and activity monitoring subsystem 50 moves, capacitance varies. Greater variances in capacitance are associated with more vigorous motion or activity by the wearer. If the individual remains motionless, the activity signal will be low or zero. Preferably, however, the actual capacitance value will be different from the condition where the individual does not wear the air sampling device.

The capacitance measuring range of a data logger, such as the SmartReader 4, may be somewhat limited to between about 180 pico farads (pF) and about 220 pF. The capacitor plates 80, 82 have a low capacitance (e.g., in a range of about 5 pF to about 10 pF). Therefore, a fixed capacitor may be connected in parallel with the plates 80, 82 to put the total capacitance in the proper range (i.e., 180–220 pF).

According to the present invention, the quantity that represents an individual's activity is the absolute value of the first time-derivative of the capacitance value (C) with time:

$$\text{Activity} \propto \left| \frac{dC}{dt} \right|$$

It is understood that the magnitude and frequency of the change in capacitance over time is an important indicator of activity.

An activity monitoring subsystem 50 according to the present invention is preferably calibrated and ranges of activity values are preferably defined. For example, activity values of 0–1 can represent when the air sampling device is not worn, values of 2–4 can represent low activity, values of 5–16 can represent moderate activity, and values greater than 16 can represent high activity.

A Fourier power spectrum of the activity signal produced by the activity monitoring subsystem 50 according to the present invention can produce amplitudes of events that occur one or more times per day. Accordingly, if a once-per-day amplitude is reasonably high, then there is a good indication that the air sampling device was worn by an individual. If such an amplitude is low, then there is a good indication that the air sampling device was not worn, or was not worn properly. High and low amplitude values can be defined by calibration and experience.

Figure 4:
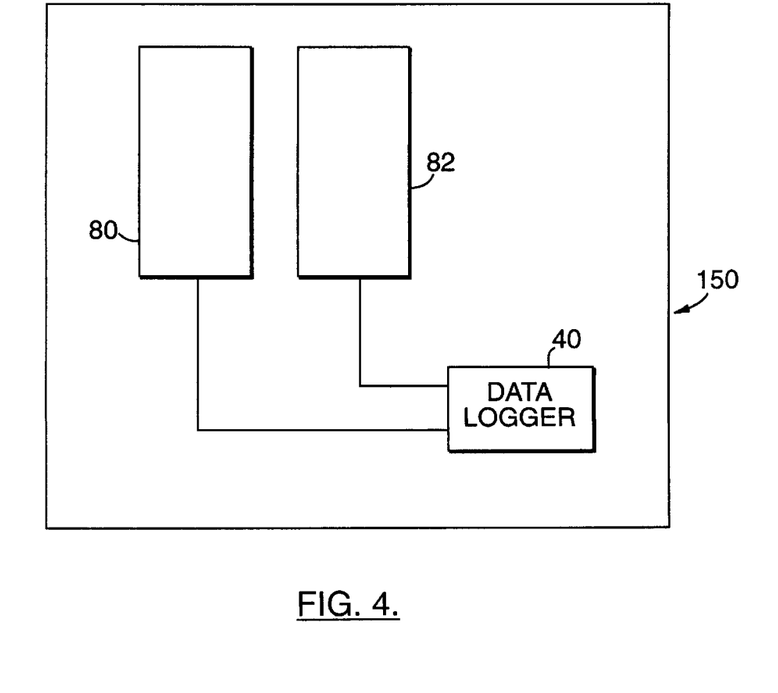
FIG. 4 illustrates a non-intrusive activity monitor for measuring the physical activity of a user, according to another embodiment of the present invention.
Figure 5:
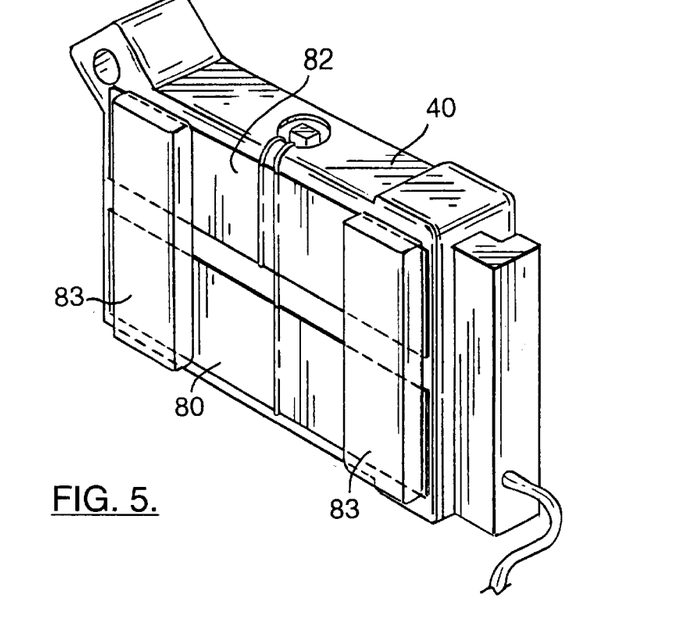
FIG. 5 illustrates a pair of adjacent capacitor plates secured to a data logger according to an embodiment of the non-intrusive activity monitor of FIG. 4.

According to another aspect of the present invention illustrated in FIG. 4, a non-intrusive activity monitor 150 may operate as a stand-alone system for measuring the physical activity of a user, independent of an air sampling system. A pair of capacitor plates 80, 82 can be used in conjunction with a data logger 40 as described above. A preferred embodiment is illustrated in FIG. 5, wherein capacitor plates 80, 82 are secured to a back portion of a data logger 40. One or more of the various channels of the data logger 40 can then be utilized to record changes in capacitance and, hence, user activity. The self-contained activity monitor 150 may be carried easily in a pocket of an individual's clothing. A pocket location can provide excellent sensitivity to motion without being intrusive to the wearer. When carried within pockets of tight fitting clothing, small spacers of foam 83 or other springy material may be utilized to maintain a flexible separation between the activity monitor 150 and the body of an individual.

Figure 6:
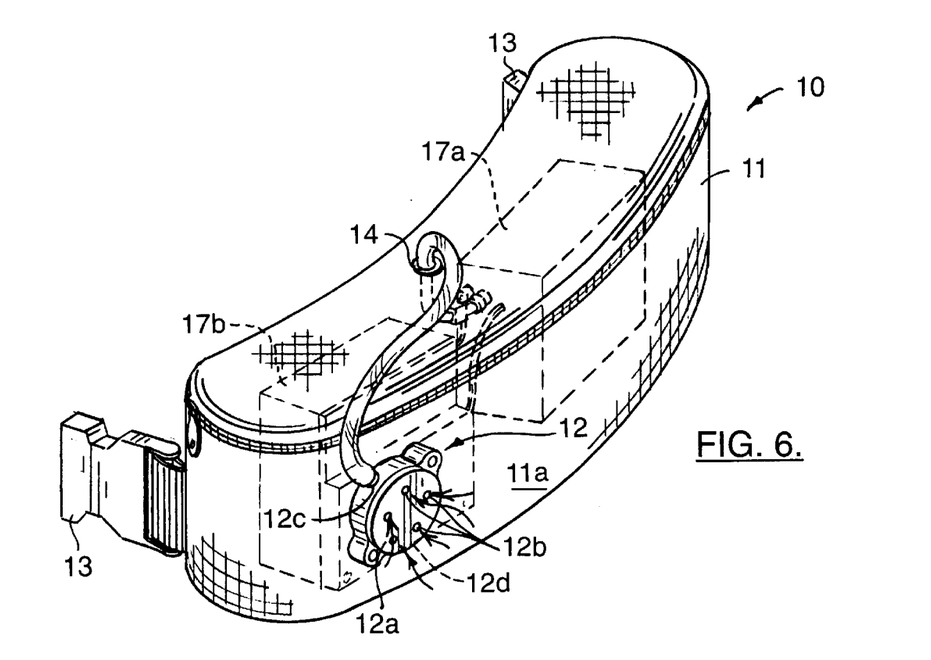
FIG. 6 illustrates a fanny pack embodiment of a portable, intermittent air sampling system according to the present invention.
Figure 7A:
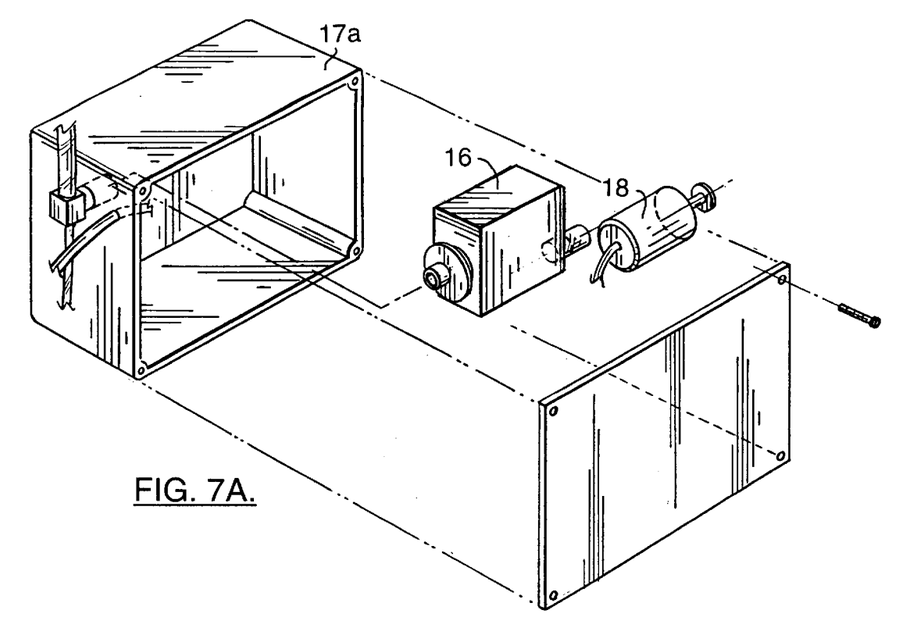
FIGS. 7A–7B illustrate the contents of various housings contained within the fanny pack embodiment of FIG. 6.
Figure 7B:
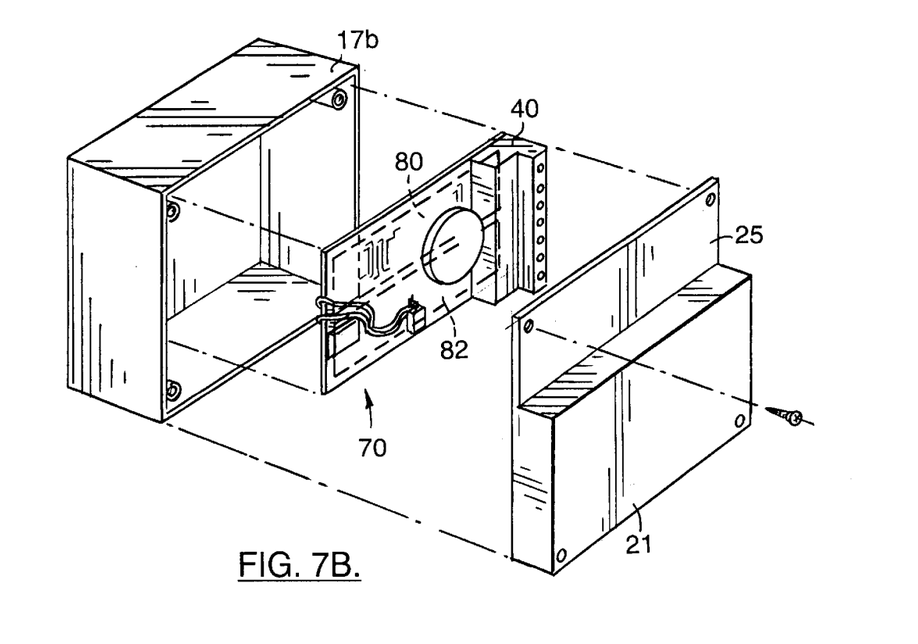

Referring now to FIG. 6 and FIGS. 7A–7B, an embodiment of a portable, intermittent air sampling system 10 is illustrated. A pack 11 is configured to be worn by a person and houses the various components of the present invention. In the illustrated embodiment, the pack 11 is a "fanny pack" that is configured to be worn around the waist of a person. The fanny pack 11 is retained around the waist of a person via a strap (not shown) and connectors 13. However, other known devices may also serve as means for retaining the pack 11 on a person. Fanny packs are well known, and need not be described further herein. In addition, it is understood that various types and configurations of packs can be utilized in accordance with the present invention. Primary objectives of the pack 11 are to be lightweight and to not inconvenience the wearer of the pack 11.

In the illustrated embodiment, a filter device 12 is secured to an outside surface 11a of the enclosure as illustrated. Housings 17a, 17b are disposed within the pack and contain various components for carrying out the present invention. Housings 17a, 17b and their contents are described below.

The illustrated filter device 12 includes a housing 12a containing a plurality of air inlets 12b and an air outlet 12c. A filter element 12d is disposed within the housing 12a and is configured to retain particles entrained within air flowing through the filter element 12d. A tube 14 connects a pump 16 located within a housing 17a with the filter device air outlet 12c.

Referring now to FIG. 7A, the housing 17a hosts a pump 16 and motor 18, as illustrated. The pump is configured to draw a predetermined volume of air into the filter device 12 and through the filter element 12d. An electric motor 18 operates the pump 16 and is powered by one or more batteries (not shown) located within a compartment 21 secured to the cover 25 of housing 17b.

Enclosed within housing 17b is a printed circuit board (PCB) 70 that hosts a data logger 40. The PCB 70 also includes electronic circuitry (not shown) for the air temperature monitoring subsystem (30, FIG. 1), the pressure drop monitoring subsystem (32, FIG. 1), the timing circuit (22, FIG. 1) for intermittent pump operation, and the battery voltage monitoring subsystem (34, FIG. 1). A pair of capacitor plates 80, 82 for monitoring the physical activity of the wearer of the pack 11 are mounted to the PCB 70, as illustrated. The capacitor plates 80, 82 serve as a transducer that changes capacitance in response to changes in distance from a conductive object (i.e., a person).

It is to be understood that the present invention is not limited to the illustrated embodiment. Various configurations and arrangements of the above components can be utilized to carry out the present invention.

Figure 8:
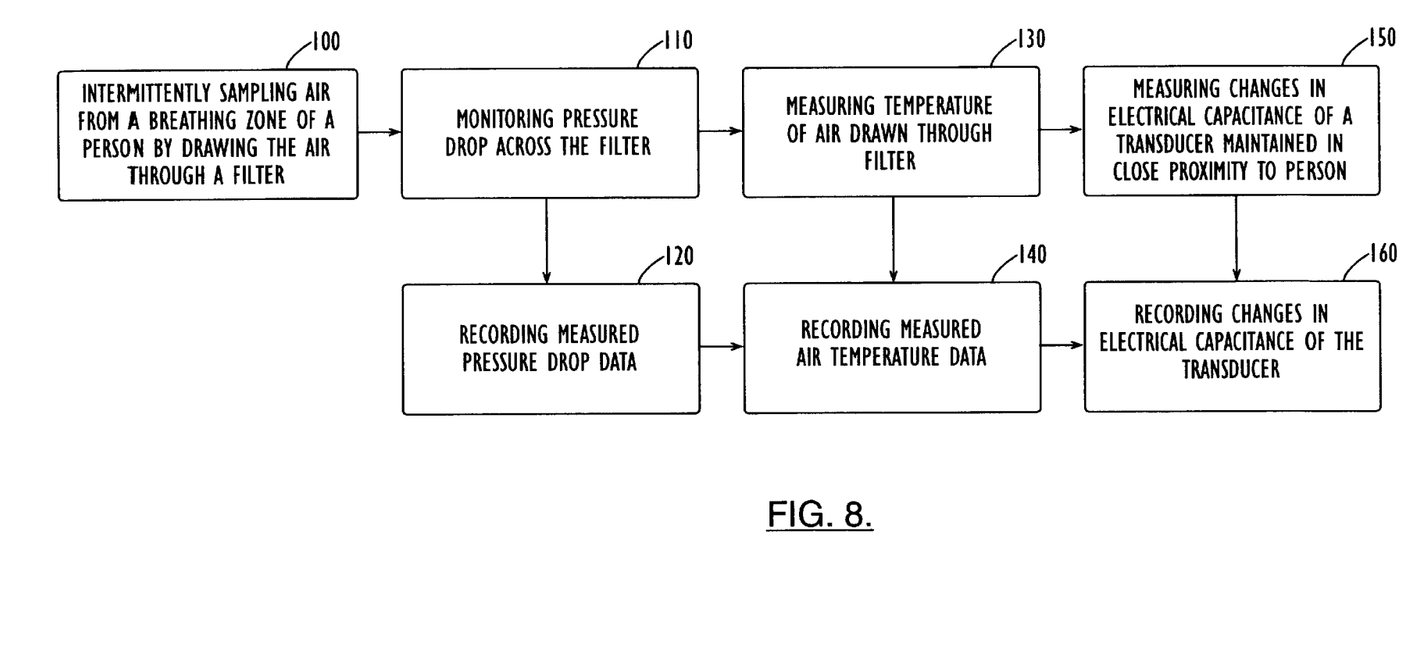
FIG. 8 illustrates steps for sampling air from the breathing zone of a person, according to an aspect of the present invention

Referring now to FIG. 8, steps for sampling air from the breathing zone of a person, according to an aspect of the present invention, are schematically illustrated. Air is intermittently sampled from a breathing zone of a person by drawing the air through a filter via a pump (Block 100). Pressure drop across the filter is measured (Block 110) and recorded (Block 120). Temperature of the air flowing through the filter is also measured (Block 130) and recorded (Block 140). Other sampling performance characteristics can be measured, as well. For example, voltage across a power supply that provides electric power to the pump motor can also be monitored. Physical activity of the person is monitored by measuring changes in electrical capacitance of a transducer maintained in close proximity to the person (Block 150) and then recorded (Block 160).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A portable air sampling system for sampling air from a breathing zone of a creature, comprising:
   a filter device, comprising:
     a housing including an air inlet in communication with the breathing zone, and an air outlet; and
     a filter element disposed within the housing that is configured to retain particles entrained within air flowing therethrough;
   a pump in fluid communication with the filter device air outlet, wherein the pump is configured to draw a predetermined volume of air into the filter device and through the filter element;
   means for intermittently activating the pump to draw the predetermined volume of air through the filter element at predetermined intervals;
   means for monitoring performance of the air sampling system; and
   means for monitoring physical activity of the creature, comprising:
     a transducer configured to change electrical capacitance in response to physical activity of the creature; and
     a data logger that records changes in electrical capacitance of the transducer.

2. A system according to claim 1 wherein the pump activating means comprises:
   an electrical motor;
   a power supply that supplies electrical power to the electrical motor; and
   a timing circuit that interrupts the supply of electrical power to the electrical motor at the predetermined intervals.

3. A system according to claim 2 wherein the means for monitoring performance of the air sampling system comprises:
   means for continuously measuring voltage across the power supply; and
   means for recording power supply voltage data within the data logger.

4. A system according to claim 1 wherein the means for monitoring performance of the air sampling system comprises:
   means for continuously measuring pressure drop across the filter; and
   means for recording measured pressure drop data within the data logger.

5. A system according to claim 1 wherein the means for monitoring performance of the air sampling system comprises:
   means for continuously measuring temperature of air drawn into the filter device; and
   means for recording air temperature data within the data logger.

6. A system according to claim 1 wherein the transducer comprises at least two adjacent capacitor plates configured to change electrical capacitance in response to a change in distance from each plate to a body of a creature.

7. A system according to claim 1 wherein the creature is a human being.

8. A portable air sampling system for sampling air from a breathing zone of a creature, comprising:
   a pack;
   means for retaining the pack on the creature;
   a filter device mounted externally to the pack, comprising:
     a housing including an air inlet in communication with the breathing zone, and an air outlet; and
     a filter element disposed within the housing that is configured to retain particles entrained within air flowing therethrough;
   a pump disposed within the pack and in fluid communication with the filter device air outlet, wherein the pump is configured to draw a predetermined volume of air into the filter device and through the filter element;
   means for intermittently activating the pump to draw the predetermined volume of air through the filter element at predetermined intervals, wherein the activating means is disposed within the pack;
   means for monitoring performance of the air sampling system, wherein the performance monitoring means is disposed within the pack; and
   means for monitoring physical activity of the creature, wherein the activity monitoring means is disposed within the pack, comprising:
     a transducer configured to change electrical capacitance in response to physical activity of the creature; and
     a data logger that records changes in electrical capacitance of the transducer.

9. A system according to claim 8 wherein the pump activating means comprises:
   an electrical motor;
   a power supply that supplies electrical power to the electrical motor; and
   a timing circuit that interrupts the supply of electrical power to the electrical motor at the predetermined intervals.

10. A system according to claim 9 wherein the means for monitoring performance of the air sampling system comprises:
    means for continuously measuring voltage across the power supply; and
    means for recording power supply voltage data within the data logger.

11. A system according to claim 8 wherein the means for monitoring performance of the air sampling system comprises:
    means for continuously measuring pressure drop across the filter; and
    means for recording measured pressure drop data within the data logger.

12. A system according to claim 8 wherein the means for monitoring performance of the air sampling system comprises:

means for continuously measuring temperature of air drawn into the filter device; and means for recording air temperature data within the data logger.

13. A system according to claim 8 wherein the transducer comprises at least two adjacent capacitor plates configured to change electrical capacitance in response to a change in distance from each plate to a body of the creature wearing the pack.

14. A system according to claim 8 wherein the pack is a fanny pack.

15. A system according to claim 8 wherein the creature is a human being.

16. A system according to claim 15 wherein the means for monitoring performance of the air sampling system comprises:

means for continuously measuring pressure drop across the filter; and means for recording measured pressure drop data within the data logger.

17. A system according to claim 15 wherein the means for monitoring performance of the air sampling system comprises:

means for continuously measuring temperature of air drawn into the filter device; and means for recording air temperature data within the data logger.

18. A system according to claim 15 wherein the means for monitoring performance of the air sampling system comprises:

means for continuously measuring voltage across the power supply; and means for recording power supply voltage data within the data logger.

19. A system according to claim 15 wherein the pack is a fanny pack.

20. A system according to claim 15 wherein the creature is a human being.

21. A portable air sampling system for sampling air from a breathing zone of a creature, comprising:

a pack;

means for retaining the pack on the creature;

a filter device mounted externally to the pack, comprising:

a housing including an air inlet in communication with the breathing zone, and an air outlet; and a filter element disposed within the housing that is configured to retain particles entrained within air flowing therethrough;

a pump disposed within the pack and in fluid communication with the filter device air outlet, wherein the pump is configured to draw a predetermined volume of air into the filter device and through the filter element;

means for intermittently activating the pump to draw the predetermined volume of air through the filter element at predetermined intervals, wherein the activating means is disposed within the pack, comprising:

an electrical motor;

a power supply that supplies electrical power to the electrical motor; and a timing circuit that interrupts the supply of electrical power to the electrical motor at the predetermined intervals;

means disposed within the pack for monitoring performance of the air sampling system;

means for monitoring physical activity of the creature, wherein the activity means is disposed within the pack, comprising:

a plurality of capacitor plates configured to change electrical capacitance in response to a change in distance from each plate to a body of the creature wearing the apparatus; and means for recording changes in electrical capacitance of the capacitor plates within a data logger.

22. A portable air sampling system for sampling air from a breathing zone of a creature, comprising:

a pack;

means for retaining the pack on the creature;

a filter device mounted externally to the pack, comprising:

a housing including an air inlet in communication with the breathing zone, and an air outlet; and a filter element disposed within the housing that is configured to retain particles entrained within air flowing therethrough;

a pump disposed within the pack and in fluid communication with the filter device air outlet, wherein the pump is configured to draw a predetermined volume of air into the filter device and through the filter element;

means for intermittently activating the pump to draw the predetermined volume of air through the filter element at predetermined intervals, wherein the activating means is disposed within the pack;

means for monitoring performance of the air sampling system, wherein the performance monitoring means is disposed within the pack, comprising:

means for continuously measuring pressure drop across the filter;

means for recording measured pressure drop data within the data logger;

means for continuously measuring temperature of air drawn into the filter device;

means for recording air temperature data within the data logger; and means for monitoring physical activity of the creature in real time, wherein the activity monitoring means is disposed within the pack, comprising:

a plurality of capacitor plates configured to change electrical capacitance in response to a change in distance from each plate to a body of the creature wearing the apparatus; and means for recording changes in electrical capacitance of the capacitor plates within the data logger.

23. A system according to claim 22 wherein the pump activating means comprises:

an electrical motor;

a power supply that supplies electrical power to the electrical motor; and a timing circuit that interrupts the supply of electrical power to the electrical motor at the predetermined intervals.

24. A system according to claim 22 wherein the pack is a fanny pack.

25. A system according to claim 22 wherein the creature is a human being.

26. A method of sampling air, comprising the steps of:

intermittently sampling air from a breathing zone of a creature, wherein air from the breathing zone is drawn through a filter via a pump;

monitoring pressure drop across the filter during the air sampling step;

monitoring physical activity of the creature during the air sampling step, comprising the step of measuring changes in electrical capacitance of a transducer maintained in close proximity to the creature; and recording measured pressure drop data and changes in electrical capacitance of the transducer.

27. A method according to claim 26 further comprising the step of measuring temperature of air drawn through the filter during the air sampling step.

28. A method according to claim 26 wherein the step of measuring changes in electrical capacitance of a transducer maintained in close proximity to the creature comprises measuring changes in electrical capacitance of a plurality of adjacent capacitor plates in response to a change in distance from each plate to the creature.

29. A method according to claim 26 wherein the creature is a human being.

\* \* \* \* \*